(12) United States Patent
Barbato et al.

(10) Patent No.: US 7,846,469 B2
(45) Date of Patent: Dec. 7, 2010

(54) REVERSIBLE INHIBITION OF SPERM RECEPTOR SYNTHESIS FOR CONTRACEPTION

(75) Inventors: Guy F. Barbato, State College, PA (US); Alexander MacDonald, North Caldwell, NJ (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 11/833,472

(22) Filed: Aug. 3, 2007

(65) Prior Publication Data

US 2008/0031926 A1   Feb. 7, 2008

Related U.S. Application Data

(60) Provisional application No. 60/821,445, filed on Aug. 4, 2006, provisional application No. 60/913,034, filed on Apr. 20, 2007.

(51) Int. Cl.
*A01N 43/54* (2006.01)
*C07D 239/42* (2006.01)
*A01N 47/28* (2006.01)
*A61K 31/17* (2006.01)

(52) U.S. Cl. ............... 424/439; 514/274; 514/588; 514/647; 514/256

(58) Field of Classification Search .............. None
See application file for complete search history.

(56) References Cited

U.S. PATENT DOCUMENTS 4,366,168 A * 12/1982 Clinton et al. .......... 514/449
4,399,151 A *  8/1983 Sjoerdsma et al. ........ 514/564
4,797,275 A      1/1989 Brooks et al.
4,981,874 A *  1/1991 Latter et al. ............ 514/682

FOREIGN PATENT DOCUMENTS

EP       0807430 A    11/1997

OTHER PUBLICATIONS

Hinsch et al. Species specificity of human and murin anti-ZP3 synthetic peptide antisera and use of antibodies for localization and use of the antibodies for localization and identification of ZP3 or ZPC domains of functional significance. Human Reproduction, vol. 14, No. 2., pp. 419-428, 1999.*
Rankin et al. Human ZP3 restores fertility in ZP3 null mice without affecting order-specific sperm binding. Development, 125, 2415-2424, 1998.*
Barbato, G.F. et al., "A practical in vitro sperm-egg binding essay that detects subfertile males", Biology of Reproduction, 58(3):686-699 (Mar. 1998).
Hurley, J.C. et al., "Poly(methyl methacrylate) synthetic grit formulations sustain the delivery of nicarbazin, a contraceptive agent, in pest waterowl", J. Controlled Release, Elsevier, Amsterdam, NL, 85(1-3):135-143 (Dec. 2002).
Johnston, J.J. et al., "Quantification of plasma and egg 4,4'0dinitrocarbanilide (DNC) residues for the efficient development of a nicarbazin-based contraceptive for pest waterfowl", Pest Management Science Feb. 2002, 58(2):197-202 (Feb. 2002).
Yoder, C.A. et al., "Effect of method of delivering nicarbazin to mallards on plasma 4,4'-dinitrocarbanilide levels and reproduction", Poultry Science, Champaign, IL, US, 85(8):1442-1448 (Aug. 2006).
Yoder, C.A. et al., "Evaluation of nicarbazin as a potential waterfowl contraceptive using mallards as a model", Poultry Science, 85(7):1275-1284 (Jul. 2006).

* cited by examiner

*Primary Examiner*—Brandon J Fetterolf
*Assistant Examiner*—Anna Pagonakis
(74) *Attorney, Agent, or Firm*—McKee, Voorhees & Sease, P.L.C.

(57) ABSTRACT

Methods and pharmaceutical compositions are disclosed for reversibly inhibiting sperm receptor activity in animals. Nicarbazin, its derivatives and modifications which retain pharmacological activity are shown to inhibit activity of zona pellucida proteins and concomitant synthesis and/or assembly of the sperm receptor on the oocyte surface necessary for fertilization. Nicarbazin is easily administered, for example by simple addition to feed of an animal and is and non-toxic to the animals, providing a safe and efficient means for controlling populations of mammals and avian species.

15 Claims, 5 Drawing Sheets

REVERSIBLE INHIBITION OF SPERM RECEPTOR SYNTHESIS FOR CONTRACEPTION

CROSS REFERENCE TO RELATED APPLICATIONS

This application claims priority under 35 U.S.C. §120 of provisional applications Ser. Nos. 60/821,445 filed Aug. 4, 2006 and 60/913,034 filed Apr. 20, 2007, which applications are hereby incorporated by reference in their entirety.

GRANT REFERENCE

This invention was made with government support under Grant No. PEN03946. The government has certain rights in the invention.

BACKGROUND OF THE INVENTION

Nicarbazin has been used for over 50 years to control coccidiosis, an infection of protozoan parasites, in domestic poultry (see review by Chapman, 2001). While the exact mode of action of is unknown, several biochemical effects have been reported. One of the most acknowledged effects of nicarbazin on cells is to cause a leakage of potassium ions across the cell membrane along with an effect on mitochondrial energy production (Long, 1978). It is unclear how either of these effects influences the parasite itself, although nicarbazin has differential effects during the life cycle of the protozoan *Eimeria*—directly inhibiting both the asexual and sexual aspects of reproduction (Danforth, 1997; Xie, 1991).

In the poultry industry, nicarbazin is commonly administered to growing, meat-type chickens (e.g., broilers). However, when mistakenly added to the feed of egg-laying chickens, depigmentation of egg-shell color and egg production drop precipitously within a matter of days (Ott et al., 1956; Sherwood et al., 1956). These older studies clearly demonstrated a drug dosage effect among broiler-breeder hens; demonstrating that lower levels of nicarbazin (<125 ppm) produced a significant reduction in hatchability of fertile eggs. Higher levels (ca. 700 ppm) eliminated egg production entirely. However, all studies demonstrated that normal hatchability and egg production returned within 7-10 days following the removal of nicarbazin from the feed.

Chapman (2001) and others (e.g., Jones et al., 1990) suggest that nicarbazin functions to reduce hatchability of chicken eggs via the creation of 'leaky membranes' within the egg. Applicants have found that the main effect of nicarbazin was to alter the structure of the oocyte membrane by altering the structure and/or assembly of the primary protein composing the membrane (i.e., zona pellucida protein C (ZPC)). ZPC is also the primary sperm receptor among birds, mice, rats, cows and humans. Which thus would make the protocol useful in other animals besides just birds.

It is an object of the present invention to provide pharmaceutical compositions and methods for contraception in mammals.

It is yet another object of the invention to provide a method of contraception for animals and in particular, mammals, that is reversible.

It is yet another object of the invention to provide a method for animal contraception that may be orally administered, by for example, addition to feed of animals.

Other objects of the invention will become apparent from the description of the invention which follow.

FIELD OF THE INVENTION

The invention is in the field of reproductive physiology. Novel contraceptive agents are disclosed based on their ability to interfere with sperm receptor synthesis.

SUMMARY OF THE INVENTION

According to the invention, nicarbazin, its derivatives and modifications which retain activity, have been found to reversibly inhibit sperm receptor synthesis by the granulosa cells (in birds) and the oocyte (in mammals). Inhibition of synthesis and/or assembly of the sperm receptor on the oocyte surface, is necessary for fertilization take place. Thus the invention encompasses a novel pharmaceutical composition for contraception in both the avian and mammalian species comprising nicarbazin, its derivatives and modifications and a pharmaceutically acceptable carrier. The contraceptive activity occurs only upon administration of the nicarbazin and is reversed with the compound is no longer present. The nicarbazin can be administered in any manner such as, by addition to feed.

The pharmaceutical composition of the invention allows for an effective contraceptive strategy that does not involve any of the traditionally accepted hormonal mechanisms of oocyte development and/or maturation.

In yet another embodiment, the invention may be used to further study the sperm receptor interaction and identify agents which modulate the same for affecting fertility in animals, by screening for agents which affect ZPC transcription or translation and either reverse or enhance the effects of nicarbazin.

DETAILED DESCRIPTION OF THE INVENTION

Applicants, have discovered a method for reversibly inhibiting the production and/or assembly of a competent sperm receptor in animals. According to the invention, applicants have identified that nicarbazin eliminated fertility and fecundity in birds as well as mammals via the inhibition of the synthesis and/or production of the primary protein making up the sperm receptor in vertebrates.

The contraceptive method is also particularly useful in countries where it is desired to reduce an animal population without killing the animals, instead, the animals, when fed nicarbazin supplemented food, simply can no longer multiply.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

As used herein the term "nicarbazin" shall be interpreted to include nicarbazin including its derivatives, modifications, homologs and the like which retain activity. Nicarbazin has been used in starter rations for several decades as an aid in the prevention of faecal and intestinal coccidiosis in broiler chickens. It may be used in combination with ionophore coccidiostatics. Chemically, it is an equimolar complex of 1,3-N,N'-bis(4-nitrophenyl)urea and 4,6-dimethyl-2(1H)-pyrimidone. These compounds are also known as 4,4'-dinitrocarbanilide and 2-hydroxy-4,6-dimethylpyrimidine, respectively (see FIG. 1). Nicarbazin is described as an electron donor-acceptor molecular complex; the sites of the interaction are the electron-poor NH amide groups of the acceptor phenylurea and the electron-rich lone pairs of the nitrogen in the pyrimidone donor ring.

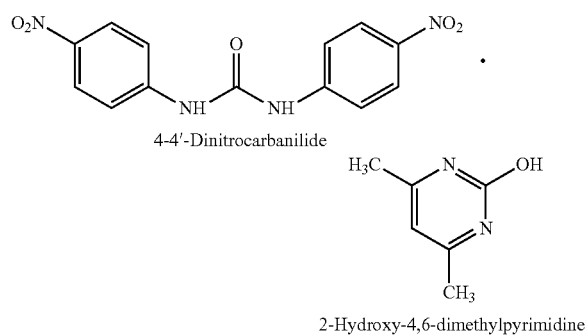

Figure 1:
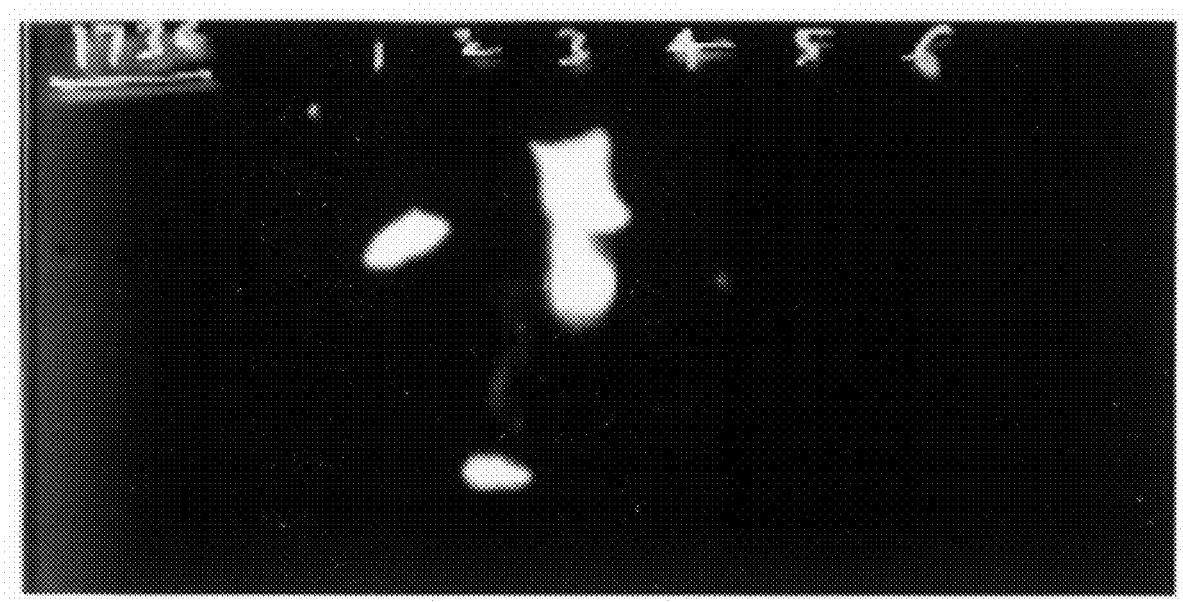
FIG. 1 is a Western blot of chicken ZPC proteins. Lanes 1=chZPC; 2=22kd chAPC, 3=granulosa cell extract; 4=1 mM nicarbazin; 5=10 mM nicarbazin' 6=100 mMnocarbazin (all cells were dead).

FIG. 1. Structures of components of nicarbazin 4-4'-Dinitrocarbanilide

2-Hydroxy-4,6-dimethylpyrimidine

Zona Pellucida Proteins and Nucleic Acids

Applicants have identified that nicarbazin inhibits zona pellucida activity by transcription and/or translation. Zona pellucida (ZP) DNA and amino acid sequences are well conserved in all mammalian species, such as mouse, chicken, pig, cow, dog, cat, marsupials, non-human primates and human and are generally available through public sources such as Genbank. Hence, the present invention contemplates the contraceptive/sterilant effectiveness of nicarbazine in heterologous (eg: porcine zona pellucida, PZP 3-a in mice) as well as in homologous( eg: canine zona pellucida, CZP-2 and CZP-3 in dogs) systems.

Pharmaceutical Compositions and Routes of Administration

Pharmaceutical compositions of the present invention comprise administering an effective amount of nicarbazin dissolved or dispersed in a pharmaceutically acceptable carrier to a subject. The phrases "pharmaceutical or pharmacologically acceptable" refers to molecular entities and compositions that do not produce an adverse, allergic or other untoward reaction when administered to an animal, such as, for example, an avian, as appropriate. The preparation of a pharmaceutical composition that contains at least one nicarbazin active ingredient will be known to those of skill in the art in light of the present disclosure, and as exemplified by Remington's Pharmaceutical Sciences, 18th Ed. Mack Printing Company, 1990, incorporated herein by reference. Moreover, for animal administration, it will be understood that preparations should meet sterility, pyrogenicity, general safety and purity standards.

A pharmaceutical composition of the present invention may comprise different types of pharmaceutically acceptable carriers depending on whether it is to be administered in solid, liquid or aerosol form, and whether it needs to be sterile for such routes of administration as injection. A pharmaceutical composition of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a subject can be determined by physical and physiological factors such as body weight, previous or concurrent therapeutic interventions, idiopathy of the animal and on the route of administration. The number of doses and the period of time over which the dose may be given may vary. The practitioner responsible for administration will, in any event, determine the concentration of active ingredient(s) in a composition and appropriate dose(s), as well as the length of time for administration for the individual subject.

In certain embodiments, pharmaceutical compositions may comprise, for example, at least about 0. 1% of an active compound. In other embodiments, the active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The nicarbazin pharmaceutical composition of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In certain aspects of the invention, nicarbazin is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

EXAMPLE 1

Nicarbazin has been used for over 50 years to control coccidiosis, an infection of protozoan parasites, in domestic poultry (see review by Chapman, 2001). While the exact mode of action of is unknown, several biochemical effects have been reported. One of the most acknowledged effects of nicarbazin on cells is to cause a leakage of potassium ions across the cell membrane along with an effect on mitochondrial energy production (Long, 1978). It is unclear how either of these effects influences the parasite itself, although nicarbazin has differential effects during the life cycle of the protozoan *Eimeria*—directly inhibiting both the asexual and sexual aspects of reproduction (Danforth, 1997; Xie, 1991).

In the poultry industry, nicarbazin is commonly administered to growing, meat-type chickens (e.g., broilers). However, when mistakenly added to the feed of egg-laying chickens, depigmentation of egg-shell color and egg production drop precipitously within a matter of days (Ott et al., 1956;

Sherwood et al., 1956). These older studies clearly demonstrated a drug dosage effect among broiler-breeder hens; demonstrating that lower levels of nicarbazin (<125 ppm) produced a significant reduction in hatchability of fertile eggs. Higher levels (ca. 700 ppm) eliminated egg production entirely. However, all studies demonstrated that normal hatchability and egg production returned within 7-10 days following the removal of nicarbazin from the feed.

Chapman (2001) and others (e.g., Jones et al., 1990) suggest that nicarbazin functions to reduce hatchability of chicken eggs via the creation of 'leaky membranes' within the egg. We hypothesized that the commonly accepted explanation of the decline in hatchability was incorrect, as it could not account for declines in either fertility or egg production at higher drug doses. Offering an alternative explanation; we further hypothesized that the main effect of nicarbazin was to alter the structure of the oocyte membrane by altering the structure and/or assembly of the primary protein composing the membrane (i.e., zona pellucida protein C (ZPC)). ZPC is also the primary sperm receptor among birds, mice, rats, cows and humans. Which thus would make the protocol useful in other animals besides just birds.

In a preliminary effort to support this hypothesis, we isolated granulosa cells from primary follicles of a laying hen, and suspended them in a simple cell culture media (1 ml medium (M)199-HEPES supplemented with Hank salts (Gibco-BRL) plus 1 ml Dulbecco modified Eagle medium (DMEM) containing 5% FBS). Nicarbazin was added to the cells at a concentration of 10 mM. The cells were then disrupted with a sonicator and proteins precipitated and heat solubilized per Barbato et al. (1998). Proteins were concentrated, separated via gel electrophoresis and western blot performed with antibodies to chicken ZPC. As can be seen in FIG. 1, nicarbazin treatment (lanes 4-6) resulted in the absence of immunoreactive ZPC (control chZPC in lanes 1 and 3).

EXAMPLE 2

Several studies were designed and executed to determine the effects of oral doses of nicarbazin on the sperm receptor in the oocyte membrane. Initially, both ducks and chickens were used to identify the main effect of nicarbazin treatment.

EXAMPLE 2.1

Figure 2:
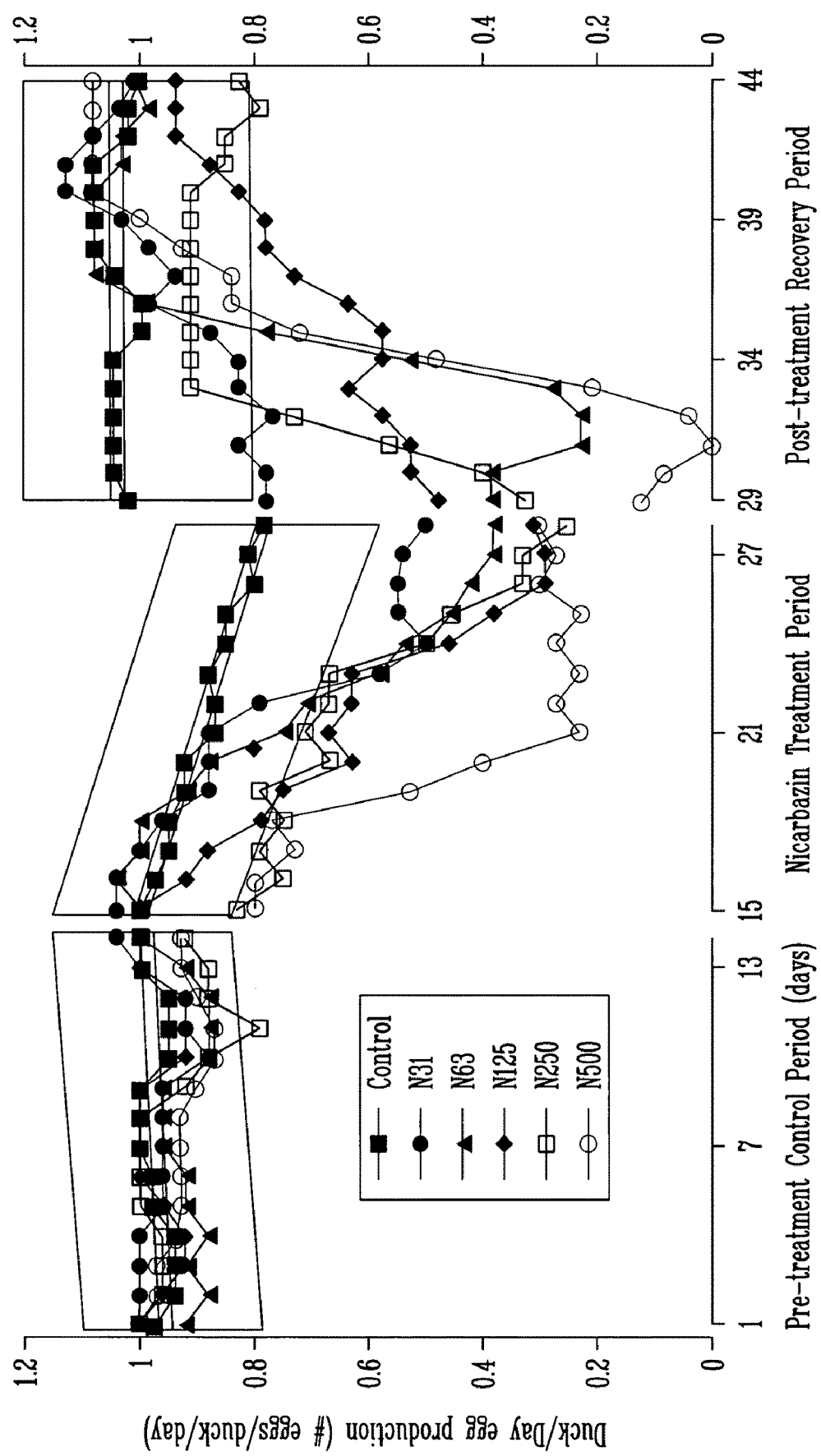
FIG. 2 shows the egg production of Pekin Ducks fed varying doses of nicarbazin. Gray represents 95% confidence intervals of the regression of the control group—any data points that fall outside this area are significantly different from the controls.]

Our first study determined the dose-response relationship for the effect of nicarbazin in reducing egg production and/or hatchability in ducks. DNC concentrations in the blood and laid eggs established a linear dose-concentration relationship with fed nicarbazin dose. (Doses used in this study were—0 mg/kg (control), 31.25 ppm, 62.5 ppm, 125 ppm, 250 ppm and 500 ppm (these doses correspond to the range of doses known to affect hatchability in chickens, Chapman, 2001). FIG. 2 illustrates the decline in egg production both pre and post-nicarbazin treatment.

Figure 3:
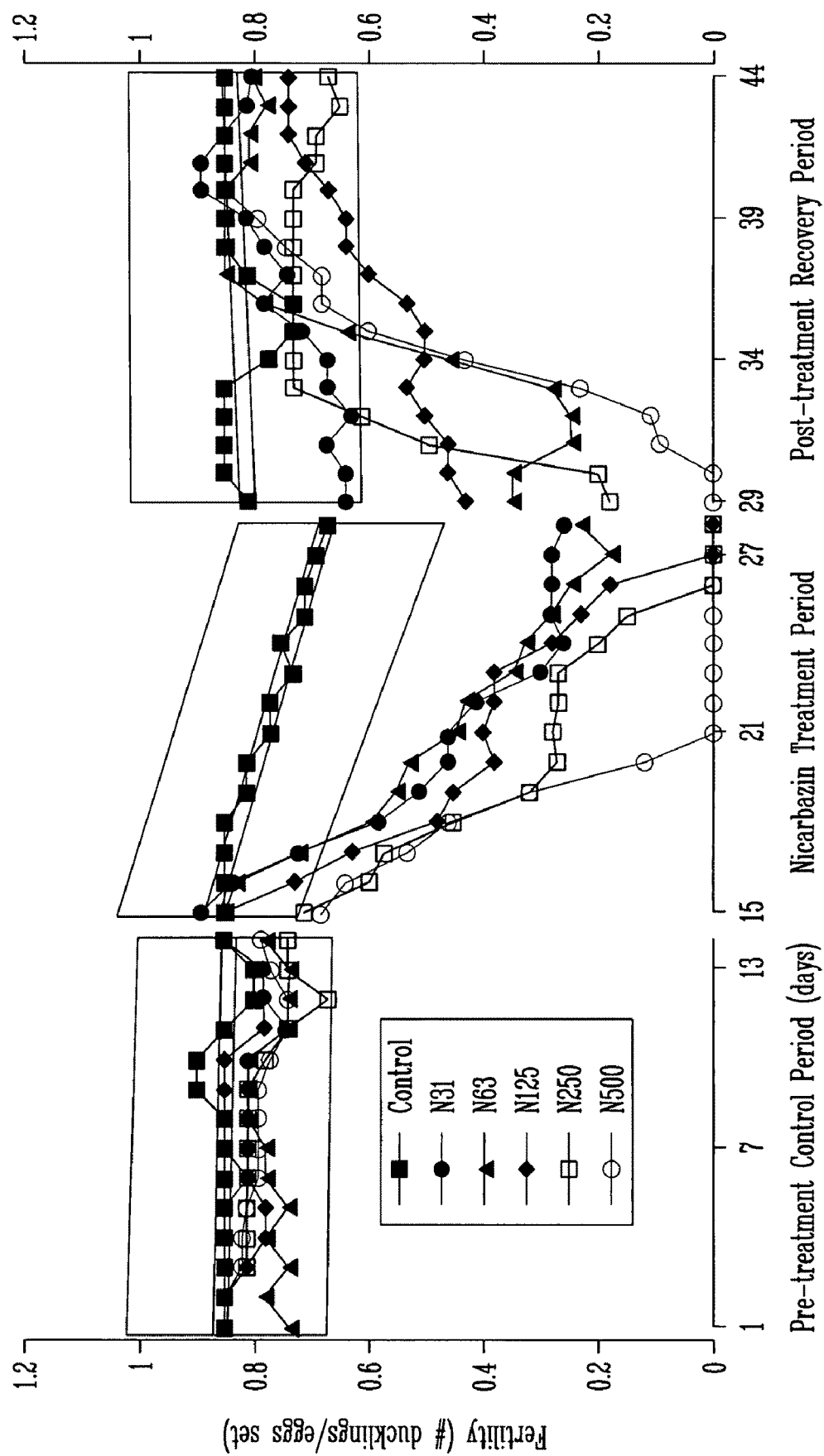
FIG. 3 depicts the fertility of laid eggs obtained from Pekin Ducks fed varying doses of nicarbazin. The gray area represents 95% confidence intervals of the regression of the control group—any data points that fall outside this area are significantly different from the controls.

Since all hens in this experiment were artificially inseminated with sperm from untreated drakes, the effects on subsequent fertility were considered to be due entirely to the effect of nicarbazin on the female ducks. FIG. 3 illustrates the profound effect of oral doses of nicarbazin on the fertility of eggs laid by treated hens. Further, upon the withdrawal of nicarbazin-treated feed, even the hens receiving the highest dose of nicarbazin returned to normal egg production and fertility within 10 days.

Figure 4:
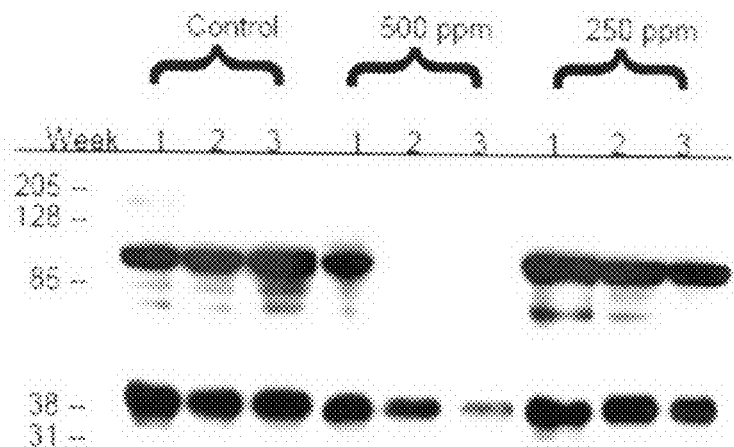
FIG. 4 shows the immunoreactive proteins (to a ZP3 antibody) from the perivitelline membrane of laid eggs from Pekin ducks fed varying doses of nicarbazin. Drug feeding began in Week 2; making Week 1 and internal control.

A subsample of eggs were collected during each week of the experiment, in order to dissect, extract and identify the ZPC in the oocyte membrane using and anti-ZPC antibody and western blotting technique. FIG. 4 illustrates that at the 500 ppm dose of nicarbazin, ZPC was undetectable after the 1st week of treatment, and remained absent thereafter. Oocyte membranes from ducks receiving the 250 ppm dose had a clear decline in the intensity of ZPC over time.

Figure 5:
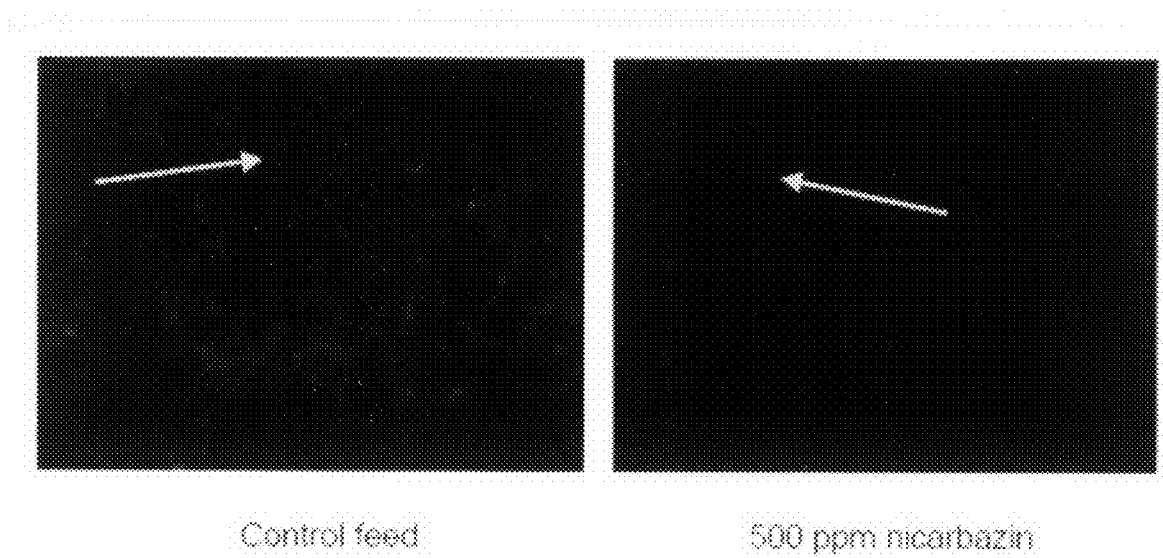
FIG. 5 demonstrates the large number of brightly stained sperm trapped in the oocyte membrane of the fertile, control egg, while the nicarbazin treated hen laid only infertile eggs with many fewer sperm (insufficient number to insure fertilization). Ducks were inseminated with 200 million sperm, overall fertility of control duck eggs was 87% (of 49 eggs set), while the 500 ppm nicarbazin ducks had a fertility of 20% (of 5 eggs set). [Images were taken at 20× magnification with DAPI fluorescent stain.]

Since there appeared to be a decrease in the amount of ZPC (the primary sperm receptor) present in the duck oocyte membranes, we reasoned that the lack of fertility in any laid eggs should be due to a decline in sperm attaching to the oocyte. FIG. 5 illustrates a pair of sample membranes from both control and nicarbazin treated ducks. Consistent with previous data from our lab (e.g., Barbato et al., 1998) 228±15 sperm/mm2 of oocyte membrane were found in eggs from control ducks, whereas there were 0±15 sperm/mm2 counted on the membranes from nicarbazin-treated ducks.

EXAMPLE 2.2

As a follow-up experiment, we fed a group of 6 laying hens the 250 ppm nicarbazin treated feed, in an attempt to reduce, but not eliminate, ZPC synthesis. Egg membranes were collected from laid eggs and the most mature follicle dissected from both treated and control hens. The membranes were fixed with osmium tetroxide, sectioned via microtome and viewed with electron microscopy.

Figure 6:
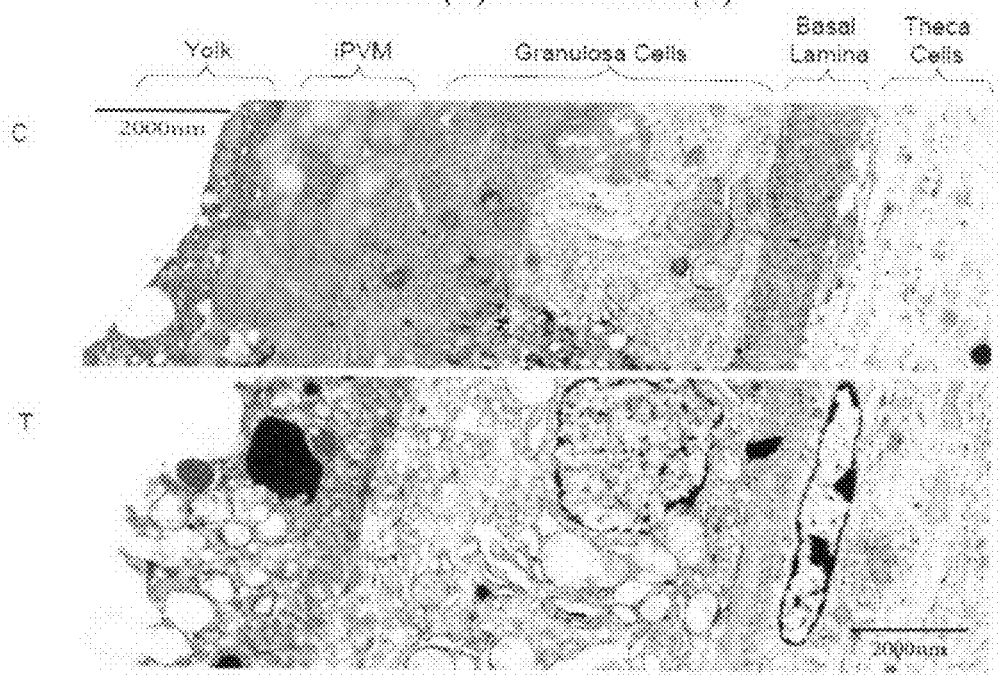
FIG. 6 is an electron micrograph of a mature follicle from control (C) and nicarbazin treated (T) hens.

FIG. 6 clearly demonstrates the reduction in width of the inner perivitelline membrane, which is made up of 85% ZPC protein. This micrograph provides direct, visual confirmation of the previously presented data: that is, that oral nicarbazin dosages reduces the ZP3 content of the oocyte membrane. Further, the reduction is of sufficient magnitude to reduce sperm binding and, hence, fertility in treated animals.

EXAMPLE 3

In an experiment performed by the World Health Organization in 1998 to evaluate the toxic effects of nicarbazin (WHO FOOD ADDITIVES SERIES 41; http/www.inchem.org). Groups of 12 male and 12 female FDRL rats were fed diets containing the phenylurea and the pyrimidone components at concentrations calculated to achieve doses of 0, 50, 150, or 300 mg/kg bw per day of the phenylurea and 0, 17, 50, or 100 mg/kg bw per day of the pyrimidone. Treatment was administered continuously during the production of two litters per generation for three successive generations. In their results section the authors remarked, "In subsequent generations, the F2a and F3a litters at the high dose had slightly fewer pups, but the effect was not reproduced in the F2b or Fib litters." In the conclusions, the authors suggested that reduced litter sizes were observed, but were inconsistent and thought to be of minor importance. However, the relative distribution of the active components of nicarbazin were significantly different that those observed in the avian species. If nicarbazin were to be re-formulated to result in similar concentrations in mammalian blood, we hypothesize that the nicarbazin-induced effect on fertility and fecundity will be observed in mammals.

EXAMPLE 3.1

Figure 7:
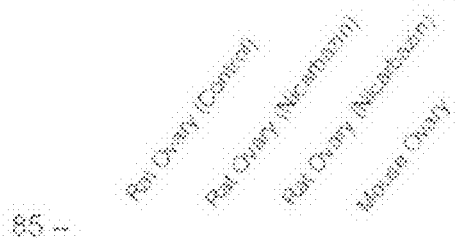
FIG. 7 is a Western Blot (using mouse ZPC monoclonal antibody) of rat ovarian tissue after 1 week of nicarbazin feeding. [mZPC-mab 1:2000; similar results obtained with dilution of 1:5000 and 1:10000. Note reduction in intensity of ZPC immunoreactive band at approx. 50 kDa.
Figure 7:
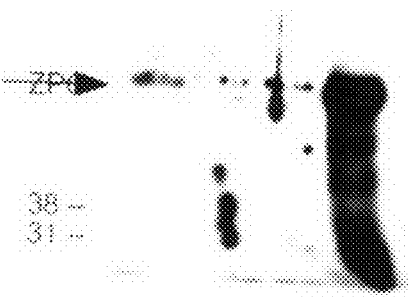

In an attempt to increase nicarbazin absorption in a mammalian species we paired nicarbazin with a typical pharmaceutical carrier, 5% propylene glycol (PGC). A 500 ppm dose was fed to 8 adult, female rats for a 7-day period, at which time the rats were killed and the ovaries removed and placed in RNAlater (to preserve protein, RNA and DNA—4 control rats were also sacrificed). Ovarian proteins and mRNA were extracted via standard laboratory protocols. FIG. 7 illustrates the results of a western blot for ZPC, using a murine monoclonal antibody (which cross-reacts with rat ZPC).

Upon finding a reduction in ZPC-immunoreactive band intensity from ovarian samples obtained from treated animals, we designed PCR primers to identify mRNA for rat ZPC. By applying the quantitative rtPCR technique we were able to estimate the number of copies of the ZPC mRNA that were present in the ovarian tissue samples. Table 1 shows the significant, 30% reduction in copy number of the ZPC gene. These data indicate that not only does nicarbazin reduce the protein expression of ZPC in rats, but also significantly reduces the transcription of the ZPC gene.

TABLE 1

Quantitative PCR results of ZP3 mRNA copy number for rats fed nicarbazin for 1 week.
[Different letters denote a significantly different t-test (P = 0.03).]
Triplicate estimate of copy number

|  | Mean | SD | OVERALL MEAN (SD) | | |
|---|---|---|---|---|---|
| Control Ovarian Tissue | | | | | |
| 1 | 1.29 | 0.27 | 1.00 | 0.23 | B |
| 2 | 0.72 | 0.15 | | | |
| 3 | 0.99 | 0.07 | | | |
| 4 | 0.99 | 0.22 | | | |
| Nicarbazin Fed Ovarian Tissue | | | | | |
| 1 | 0.47 | 0.06 | 0.71 | 0.21 | A |
| 2 | 0.95 | 0.21 | | | |
| 3 | 0.75 | 0.05 | | | |
| 4 | 0.95 | 0.33 | | | |
| 5 | 0.50 | 0.05 | | | |
| 6 | 0.85 | 0.20 | | | |
| 7 | 0.77 | 0.02 | | | |

EXAMPLE 3.2

The indirect biochemical evidence in the previous section led us to attempt a direct feeding experiment with mice. In this case, mice were fed a 0.5% nicarbazin diet (containing 5% propylene glycol). In addition, 7.5% peanut butter was added to the diet to increase palatability. Ten mating pairs of mice were given access to the diet for 4-5 hrs over a 2 period. During this period non-treated mating pairs had a conception rate of 90%, averaging 6 pups per litter. Treated mice resulted in only a single pregnancy, having 2 pups (10% conception rate having 0.2 pups/litter). The pups were completely healthy, with no sign of teratogenic effects. After removal of the treated feed all previously treated mice were mated and conceived normal litters over the next month.

REFERENCES

Barbato, G. F., P. Cramer and R. H. Hammerstedt. (1998) Evaluation of an in vitro sperm-egg binding assay assessing male infertility. Biology of Reproduction 58:686-699.
Chapman, H. D. (2001). Use of anticoccidial drugs in broiler chickens in the USA: analysis for the years 1995 to 1999. Poult Sci 80(5):572-80.
Danforth, H. D., K. Watkins, et al. (1997). Evaluation of the efficacy of *Eimeria maxima* oocyst immunization with different strains of day-old broiler and roaster chickens. Avian Dis 41(4): 792801.
Jones, J. E., J. Solis, B. L. Hughes, D. J. Castaldo and J. E. Toler (1990) Reproduction responses of broiler-breeders to anticoccidial agents. Poultry Sci. 69:27-36.
Long, P. L., K. N. Boorman, et al. (1978). Avian coccidiosis: proceedings of the thirteenth poultry science symposium, 14-16th Sep., 1977. [S.1.], British Poultry Science, ltd.
Ott, W. H., S. Kuna, C. C. Porter, A. C. Cuckler and D. E. Fogg (1956) Biological studies on nicarbazin, a new anticoccidial agent. Poultry Sci. 35:1355-1367.
Sherwood, D. H., T. T. Milby and W. A. Higgins (1956) The effect of nicarbazin on reproduction in White Rock breeder hens. Poultry Sci. 35:1014-1019.
Xie, M. Q., T. Fukata, et al. (1991). Evaluation of anticoccidial drugs in chicken embryos. Parasitol Res 77(7):595-9.

EXAMPLE 4

According to the invention, nicarbazin specifically influences the expression of the zona pellucida 3 gene and protein in vertebrates. It is expected that other homologs of the ZP3 gene will also be negatively affected by nicarbazine. For example, there is an insect homolog of ZP3 that is a structural component of the wing vein. Nicarbazin interferes with the expression of the insect homolog in the same manner as the vertebrate Gene.

In a quick experiment, 3-5% nicarbazin preparation was added to the media (food) in fruit fly vials using ethanol as a carrier (since fruit flies are attracted to ethanol). At the high dose (5%), the fruit fly eggs did not hatch. At 3%, the flies hatched—but, had deformed wings and could not fly.

What is claimed:
1. A method of reversibly inhibiting sperm receptor synthesis and assembly in animals comprising:
   administering to said non-humans in need of contraception an effective amount of nicarbazin and a carrier, inhibiting zona pellucida protein C (ZPC) in said animals, measuring ZPC, and stopping administration to said animals to reversibly restore ZPC in said animals.
2. The method of claim 1 wherein said administration is selected from the group consisting of: intravenously, intradermally, intraarterially, intraperitoneally, intranasally, intravitreally, intravaginally, intrarectally, topically, intramuscularly, intraperitoneally, subcutaneously, mucosally, intrapericardially, orally, topically, locally, inhalation (e.g., aerosol inhalation), injection, infusion, and continuous infusion.
3. The method of claim 2 wherein said administration is orally.
4. The method of claim 1 wherein said non-human is an avian.
5. The method of claim 4 wherein said avian is a chicken.
6. The method of claim 4 wherein said avian is a duck.
7. The method of claim 1 wherein said animal is a non-human.
8. The method of claim 7 wherein said non-human is a rat.
9. The method of claim 7 wherein said non-human is a mouse.
10. The method of claim 1 wherein said carrier is polyethylene glycol.
11. The method of claim 1 wherein said administration is by combining said nicarbazin with food.
12. The method of claim 11 wherein said non-human is a rat.
13. The method of claim 11 wherein said non-human is a mouse.

14. The method of claim 1 further comprising measuring said ZPC inhibition.

15. A method of inhibiting sperm receptor synthesis and assembly in non-humans comprising:
administering to said non-humans in need of contraception an effective amount of nicarbazin and a carrier;
inhibiting zona pellucida protein C (ZPC) in said non-humans; and
stopping administration to said non-humans to reversibly restore ZPC in said animals to restore fertility and allow said non-humans measuring ZPC to produce offspring.

* * * * *

UNITED STATES PATENT AND TRADEMARK OFFICE
CERTIFICATE OF CORRECTION

| | | |
|---|---|---|
| PATENT NO. | : 7,846,469 B2 | Page 1 of 1 |
| APPLICATION NO. | : 11/833472 | |
| DATED | : December 7, 2010 | |
| INVENTOR(S) | : Guy F. Barbato et al. | |

It is certified that error appears in the above-identified patent and that said Letters Patent is hereby corrected as shown below:

Column 12, Claim 15, line 2
DELETE: After humans; "and"
ADD on new line; After humans;
--measuring ZPC; and--

Column 12, Claim 15, line 4
DELETE: "animals"
ADD: --non-humans--

Column 12, Claim 15, line 5
DELETE: "measuring ZPC"

Signed and Sealed this
First Day of March, 2011

David J. Kappos
*Director of the United States Patent and Trademark Office*

UNITED STATES PATENT AND TRADEMARK OFFICE
CERTIFICATE OF CORRECTION

PATENT NO. : 7,846,469 B2 Page 1 of 1
APPLICATION NO. : 11/833472
DATED : December 7, 2010
INVENTOR(S) : Guy F. Barbato et al.

It is certified that error appears in the above-identified patent and that said Letters Patent is hereby corrected as shown below:

Cover Page, item (73) should read as follows:
ADD: After Assignee: The Penn State Research Foundation,
University Park, PA (US) --; and Pharma Science, Inc.
North Caldwell, NJ (US)--

Signed and Sealed this
Fourteenth Day of June, 2011

David J. Kappos
*Director of the United States Patent and Trademark Office*